United States Patent
Rao et al.

(10) Patent No.: US 8,288,568 B2
(45) Date of Patent: Oct. 16, 2012

(54) PROCESS FOR THE PREPARATION OF ESCITALOPRAM

(75) Inventors: Dharmaraj Ramachandra Rao, Maharashtra (IN); Rajendra Narayanrao Kankan, Maharashtra (IN); Dilip Ramdas Birari, Maharashtra (IN); Manjinder Singh Phull, Maharashtra (IN)

(73) Assignee: Cipla Limited, Mumbai (IN)

( * ) Notice: Subject to any disclaimer, the term of this patent is extended or adjusted under 35 U.S.C. 154(b) by 291 days.

(21) Appl. No.: 12/600,011

(22) PCT Filed: May 16, 2008

(86) PCT No.: PCT/GB2008/001686
§ 371 (c)(1),
(2), (4) Date: Jan. 25, 2010

(87) PCT Pub. No.: WO2008/142379
PCT Pub. Date: Nov. 27, 2008

(65) Prior Publication Data
US 2010/0204493 A1    Aug. 12, 2010

(30) Foreign Application Priority Data
May 18, 2007  (IN) .......................... 941/MUM/2007

(51) Int. Cl.
*C07D 307/87* (2006.01)
(52) U.S. Cl. ..................................... 549/467
(58) Field of Classification Search ................... 549/467
See application file for complete search history.

(56) References Cited

U.S. PATENT DOCUMENTS
4,136,193 A    1/1979    Bogeso et al.

FOREIGN PATENT DOCUMENTS
EP    0347066 A1    12/1989
WO    2008142379 A2    11/2008
WO    2008142379 A3    11/2008

OTHER PUBLICATIONS

Foreign communication from the priority application—International Search Report and Written Opinion, PCT/GB2008/001686, Feb. 13, 2009, 17 pages.
Madsen, Jacob, et al., "Gas phase production of [11C]methyl iodide-d3 Synthesis and biological evaluation of S-[N-methyl-11C]citalopram and deuterated analogues," Journal of Labelled Compounds and Radiopharmaceuticals, 2004, vol. 47, pp. 335-348, Wiley Interscience, John Wiley & Sons Ltd., XP009108552.
Foreign communication from the priority application—International Preliminary Report on Patentability, PCT/GB2008/001686, Dec. 3, 2009, 11 pages.

*Primary Examiner* — Taofiq A Solola
(74) *Attorney, Agent, or Firm* — Conley Rose, P.C.; Rodney B. Carroll

(57) ABSTRACT

The present invention provides a novel process for the preparation of a compound of Formula III, and novel processes for preparing escitalopram using the compound of Formula III.

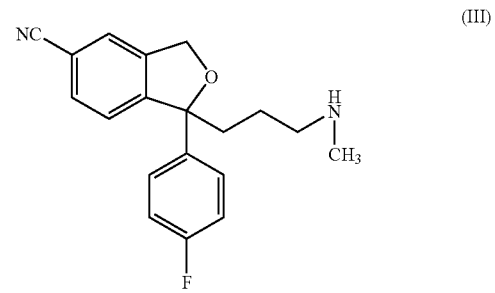

(III)

22 Claims, No Drawings

PROCESS FOR THE PREPARATION OF ESCITALOPRAM

CROSS-REFERENCE TO RELATED APPLICATIONS

This application is a filing under 35 U.S.C. 371 of International Application No. PCT/GB2008/001686 filed May 16, 2008, entitled "Process for the Preparation of Escitalopram," claiming priority of Indian Patent Application No. 941/MUM/2007 filed May 18, 2007, which applications are incorporated by reference herein in their entirety.

FIELD OF THE INVENTION

The present invention relates to a process for the preparation of a pharmaceutically useful compound, namely escitalopram.

BACKGROUND OF THE INVENTION

Citalopram is a well-known antidepressant drug and is chemically known as 1-[3-(dimethylamino)propyl]-1-(4-fluorophenyl)-1,3-dihydroisobenzofuran-5-carbonitrile. It is a selective, centrally acting serotonin (5-hydroxytryptamine; 5-HT) reuptake inhibitor, accordingly having antidepressant activities.

Citalopram was first disclosed in a German patent DE 2,657,013, corresponding to U.S. Pat. No. 4,136,193. A process for preparation of citalopram from the corresponding 5-bromo-derivative by reaction with cuprous cyanide in a suitable solvent and by alkylation of 5-bromo-phtalane is disclosed in DE 2,657,013.

Escitalopram is a pure S-enantiomer (single isomer) of the racemic citalopram.

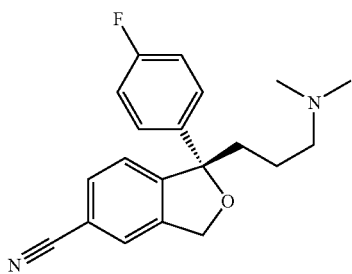

Escitalopram is at least 100 fold more potent than the R-enantiomer with respect to inhibition of 5-HT reuptake and inhibition of 5-HT neuronal firing rate and is widely used as an antidepressant.

Escitalopram and processes for its preparation were first disclosed in EP 347066. The failure of previous attempts to crystallize diastereomeric salts of citalopram enantiomers has been acknowledged in EP 347066. The aforementioned European patent discloses two processes which provide a solution to the problem of obtaining diastereomeric salts of citalopram enantiomers by employing a racemic diol compound of Formula A as a starting material.

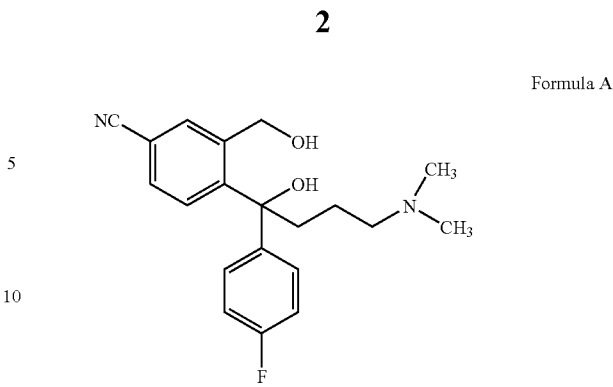

Formula A

In accordance with a first process as disclosed in EP 347066, the diol is reacted with an enantiomerically pure acid derivative, such as (+)- or (−)-α-methoxy-α-trifluoromethylphenylacetyl chloride to form a mixture of diastereomeric esters, which are separated by HPLC or fractional crystallization, whereupon the ester with the correct stereochemistry is enantioselectively converted into escitalopram.

In accordance with a second process as disclosed in EP 347066, the diol of Formula A is separated into the enantiomers by stereoselective crystallization with an enantiomerically pure acid such as (+)-di-p-toluoyltartaric acid, whereupon the S-enantiomer of the diol of the Formula I is enantioselectively converted to escitalopram.

Several other different processes for the preparation of escitalopram have been reported. However, all the hitherto reported processes for preparation of escitalopram employ a plurality of reagents and involve methods steps which make the overall processes uneconomical. Furthermore, the aforesaid reported processes do not give high purity enantiomers of citalopram. There is therefore a need for an economical process for the preparation of escitalopram that results in products in high yield with high purity.

SUMMARY OF THE INVENTION

According to a first aspect of the present invention, there is provided a process for preparing a compound of Formula III

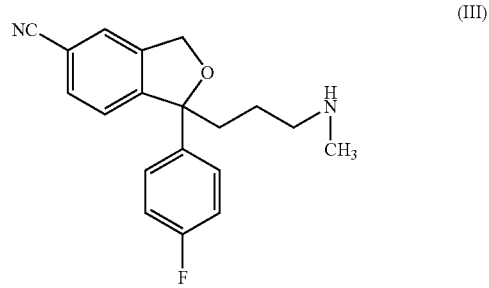

(III)

comprising demethylating citalopram of Formula IV

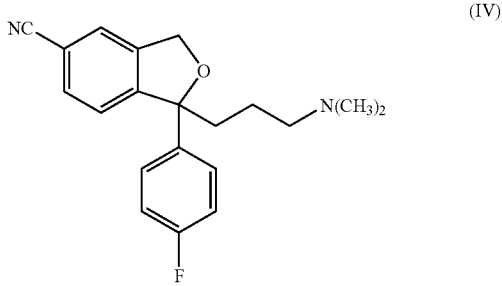

(IV)

in the presence of a demethylating agent.

In an embodiment, the demethylating agent is a chloroformate. Suitably, the chloroformate is an alkyl-, aryl-, substituted-alkyl- or substituted-aryl-chloroformate, preferably 1-chloroethylchloro formate.

Preferably, demethylation is carried out using a chloroformate, such as 1-chloroethylchloroformate, in the presence of a base such as Hünig's base (i.e. N,N-diisopropylethylamine) to form a carbamate intermediate followed by cleavage of the carbamate to yield the intermediate compound III.

Suitably, the solvent employed for carbamate formation is an inert solvent, for example toluene, EDC (ethylene dichloride or 1,2-dichloroethane), MDC (methylene dichloride or 1,2-dichloromethane), xylene; preferably toluene or MDC; most preferably MDC.

The cleavage of the carbamate may comprise hydrolysis. The hydrolysis may be carried out by refluxing the carbamate in an alcohol, for example, methanol, ethanol, isopropyl alcohol, or butanol.

According to a second aspect of the present invention, there is provided a process for preparing a compound of Formula III comprising demethylating a cyano diol compound of Formula A

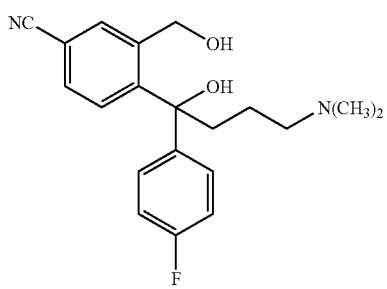

(A)

to obtain a compound of Formula VI

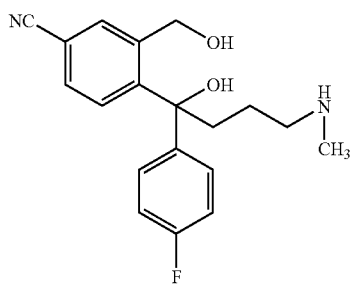

(VI)

and cyclizing the compound of Formula VI to obtain the compound of Formula III.

In an embodiment, the demethylating agent is selected from: a chloroformate, such as an alkyl, aryl or substituted alky or substituted aryl chloroformate, or thio chloro formate, to form a carbamate; K[Fe(CN)$_6$]; acetone-DEAD/NH$_4$Cl-MeOH; photolytic using Rose Bengal (an alkali metal salt of 4,5,6,7-tetrachloro-2',4',5',7'-tetraiodofluorescein) as a photosensitizing catalyst; H$_2$O$_2$—H$^+$/FeSO$_4$; and cyanogen bromide followed by cleavage of the resultant cyanamide (the Braun reaction). Reaction with a dialkyl azodicarboxylate followed by hydrolysis has also been used to effect the demethylation.

Preferably, demethylation is carried out using 1-chloroethylchloroformate in the presence of a base such as Hünig's base (i.e. N,N-diisopropylethylamine) to form a carbamate intermediate followed by cleavage of the carbamate to yield the intermediate compound VI.

Suitably, the solvent employed for carbamate formation is an inert solvent, for example toluene, EDC (ethylene dichloride or 1,2-dichloroethane), MDC (methylene dichloride or 1,2-dichloromethane), xylene; preferably toluene or MDC; most preferably MDC.

The cleavage of the carbamate may comprise hydrolysis. The hydrolysis of the carbamate may be carried out by refluxing in an alcohol, for example, methanol, ethanol, isopropyl alcohol, or butanol.

The cyclization of intermediate compound VI may be carried out in the presence of a an acid or a combination of mesyl chloride and triethylamine. Optionally, the acid is sulphuric acid, para toluene sulphonic acid, methane sulphonic acid, phosphoric acid, or hydrochloric acid.

The cyclization reaction using the acid may be carried out in the presence of water, a water miscible solvent, or a mixture thereof. The water miscible solvent may be an alcohol or a ketone.

According to a third aspect of the present invention, there is provided a process for preparing a compound of Formula II comprising resolving a mixture of the (S)- and (R)-enantiomers of the compound of Formula III in the presence of a resolving agent.

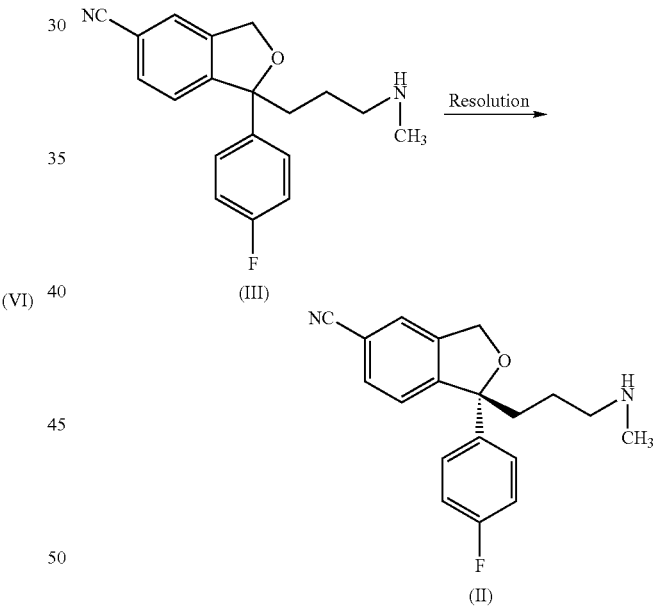

In an embodiment, the resolving agent is an acid, typically a carboxylic acid. Preferably, the acid is enantiomerically pure. The preferred acid is enantiomerically pure di-para toluoyl L-tartaric acid.

The acid may be present in a solvent such as an alcohol or an alcohol-water mixture, preferably an alcohol-water mixture. The alcohol may be methanol, ethanol, n-propanol, isopropanol, or butanol.

Preferably, the acid selectively reacts with the desired enantiomer (the S-enantiomer) present in the mixture of enantiomers of the compound of Formula III to form an acid addition salt of the S-enantiomer of the compound of Formula III. Thus, the resolution may comprise forming a salt of the S-enantiomer of the compound of Formula III with the acid and converting the salt to the free base, i.e. the compound of Formula II. The conversion to the free base may comprise reaction with a base, such as an alkali metal hydroxide, for example sodium hydroxide. In an embodiment, the salt of compound III is purified, for example by crystallization or recrystallization, prior to being converted to the free base.

Typically, the resolution is carried out by reacting compound III with 1 molar equivalence of the carboxylic acid such as di-para toluoyl L-tartaric acid.

Alternatively, the resolution may be carried out by reacting compound III with a mixture of 0.5 molar equivalence of the carboxylic acid (relative to compound III) and 0.5 molar equivalence (relative to compound III) of an inorganic acid, for example, hydrochloric acid. Preferably, the resolution is carried out in the presence of di-para toluoyl L-tartaric acid and hydrochloric acid, most preferably 0.5 molar equivalence of di-para toluoyl L-tartaric acid and 0.5 molar equivalence of hydrochloric acid.

The acid(s) may be present in a solvent such as water, alcohol, a water-alcohol mixture, or a mixture of alcohols. The or each alcohol may be, for example, methanol, ethanol, isopropyl alcohol, or butanol. Preferably, the resolution is carried out in the presence of a water-alcohol mixture.

In an embodiment, the compound of Formula III is prepared according to a process described above in the first or second aspects of the present invention.

According to another aspect of the present invention, there is provided a process for preparing escitalopram or a pharmaceutically acceptable salt thereof, which process comprises preparing a compound of Formula II by a process as described above, methylating the compound of Formula II in the presence of a methylating agent, and optionally converting the escitalopram to the salt thereof.

In an embodiment, the methylating agent is selected from the group consisting of a combination of formaldehyde and formic acid, a combination of paraformaldehyde and sodium borohydride mixture and a combination of a methyl halide with a base, preferably Hünig's base. The halide may be chloride, bromide, or iodide.

In an embodiment, methylation is carried out using a formaldehyde/formic acid combination in the presence of water, a water miscible solvent, or a mixture thereof.

In another embodiment, methylation is carried out using a paraformaldehyde/sodium borohydride combination in the presence of a solvent such as an alcohol, for example methanol, ethanol, isopropyl alcohol or butanol. The reaction is preferably carried out below 30° C., more preferably below 10° C.

Escitalopram I obtained by the process of the present invention may be further converted to a suitable acid addition salt such as, for example, mesylate, besylate, maleate, citrate, tartarate, oxalate, lactate, gluconate, hydrobromide, sulphate, and nitrate. Preferably, escitalopram I is converted to its oxalate salt.

According to further aspects of the present invention, there is provided compound III prepared by a process as described above and compound II prepared by a process as described above.

There is also provided by the present invention, escitalopram or a salt thereof, particularly the oxalate salt of escitalopram, prepared by a process as described above.

According to another aspect of the present invention, there is provided a pharmaceutical composition comprising escitalopram or a salt thereof, particularly the oxalate salt of escitalopram, prepared by a process as described above, together with one or more pharmaceutically acceptable excipients. Such excipients are well known to those skilled in the art.

According to another aspect of the present invention, there is provided the use of escitalopram or a salt thereof, particularly the oxalate salt of escitalopram, prepared by a process as described above in medicine.

According to another aspect of the present invention, there is provided the use of escitalopram or a salt thereof, particularly the oxalate salt of escitalopram, prepared by a process as described above in the treatment of depression.

According to another aspect of the present invention, there is provided a method of treating depression in a patient in need of such treatment, which method comprises administering to the patient a therapeutically effective amount of escitalopram or a salt thereof, particularly the oxalate salt of escitalopram, prepared by a process as described above.

DETAILED DESCRIPTION OF THE INVENTION

In accordance with the invention as herein described, there is provided a process for preparation of escitalopram which is economical, fast and which results in high purity enantiomers.

An embodiment of a process for the preparation of escitalopram in accordance with the present invention is exemplified in Scheme 1.

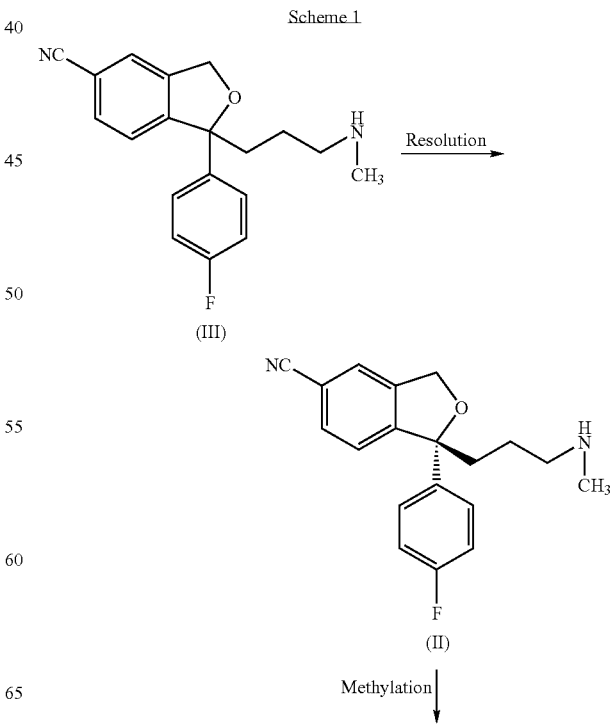

NC
[structure]
N(CH₃)₂

F (I)

The compound of Formula III is one of the hitherto unreported intermediates useful in the process for the preparation of escitalopram as described herein. The compound of Formula III may be resolved using an enantiomerically pure acid, typically, di-para toluoyl L-tartaric acid in alcohols, preferably an alcohol-water mixture to obtain a di-para toluoyl tartrate salt of compound of Formula II which may then be converted to a base.

Typically, the resolution is carried out by reacting compound III with 1 equivalence of an enantiomerically pure carboxylic acid such as di-para toluoyl L-tartaric acid.

Alternatively, the resolution may be carried out by reacting compound III with a mixture of 0.5 equivalence of an enantiomerically pure carboxylic acid and 0.5 equivalence of an inorganic acid, for example hydrochloric acid. When 0.5 equivalence of enantiomerically pure carboxylic acid is used alone, the preferred salt of the optically pure compound II does not precipitate out due to undesired isomer. However, when 0.5 equivalence of inorganic acid is employed in addition, the undesired isomer of Formula III, preferentially reacts with the inorganic acid and remains in the solution, which causes precipitation of the carboxylic acid salt of the desired isomer of Formula II.

The acid may be present in a solvent such as water, alcohol, for example, methanol, ethanol, isopropyl alcohol, or butanol. The solvent may be present in pure form, in a mixture of alcohols, in water, or in a mixture of water and alcohol. Preferably, the resolution is carried out in the presence of a water-alcohol mixture.

The compound of Formula II may be further methylated using suitable methylating agents to obtain escitalopram I which may then be converted to its pharmaceutically acceptable acid addition salt.

In an embodiment, a suitable methylating agent is selected from the group consisting of formaldehyde/formic acid, paraformaldehyde/sodium borohydride and methyl halide with a base, preferably Hünig's base. The halide may be chloride, bromide, or iodide.

In one embodiment, methylation is carried out using formaldehyde/formic acid in the presence of water, a water miscible solvent, or a mixture thereof.

In another embodiment, methylation is carried out using paraformaldehyde/sodium borohydride in the presence of a solvent such as an alcohol, for example, methanol, ethanol, isopropyl alcohol, or butanol. The reaction is preferably carried out below 30° C., more preferably below 10° C.

Escitalopram I obtained by the process of the present invention may be further converted to suitable acid addition salts such as, for example, mesylate, besylate, maleate, citrate, tartarate, oxalate, lactate, gluconate, hydrobromide, sulphate, and nitrate. Preferably, escitalopram I is converted to its oxalate salt.

According to another aspect of the present invention, there is provided processes for preparing a compound of Formula III as exemplified in Scheme 2.

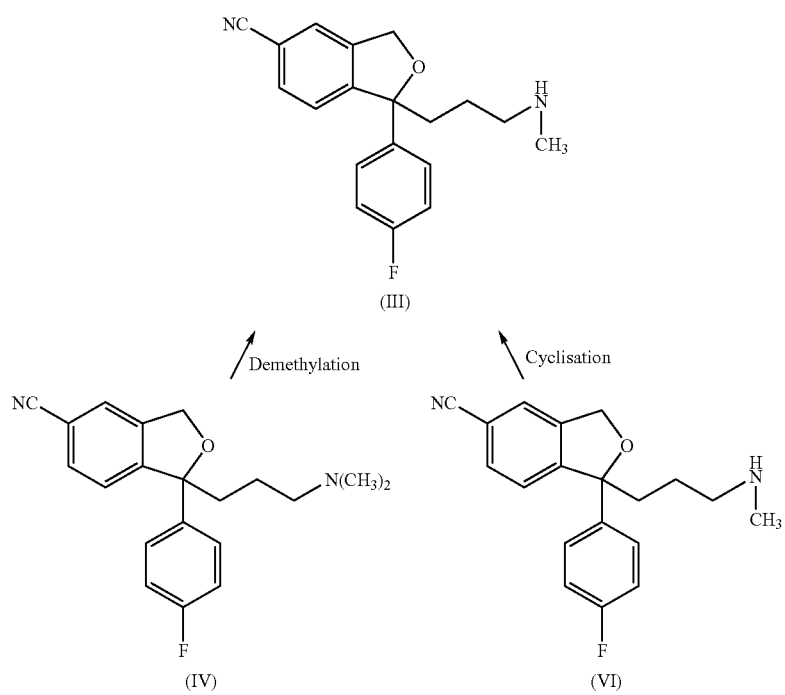

↑ Demethylation

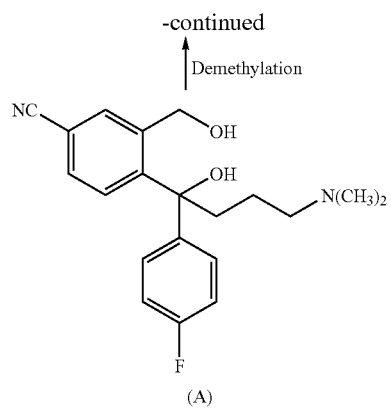

(A)

In one embodiment, citalopram, the compound of Formula IV is demethylated using a suitable demethylating agent such as a chloroformate, for example, an alkyl, aryl or substituted alky or substituted aryl chloroformate, preferably 1-chloro ethyl chloroformate. The demethylation is suitably carried out in a suitable organic solvent to obtain desmethyl citalopram of Formula III.

Alternatively, the compound of Formula III may be prepared by an alternate process wherein a cyanodiol compound of Formula A is subjected to demethylation to obtain a compound of Formula VI, which may then be cyclized, for example under acidic conditions, to afford a compound of Formula III.

Suitably, the demethylating agent employed is selected from: a chloroformate, such as an alkyl, aryl or substituted alky or substituted aryl chloroformate, or thio chloro formate; K [Fe (CN)$_6$]; acetone-DEAD/NH$_4$Cl-MeOH; photolytic using Rose Bengal (an alkali metal salt of 4,5,6,7-tetrachloro-2',4',5',7'-tetraiodofluorescein) as a photosensitizing catalyst; H$_2$O$_2$—H$^+$/FeSO$_4$; and cyanogen bromide followed by cleavage of the resultant cyanamide (the Braun reaction). Reaction with a dialkyl azodicarboxylate followed by hydrolysis has also been used to effect the demethylation. Reaction of compound A with a chloroformate results in a carbamate compound VI.

More preferably, demethylation is carried out using 1-chloro ethyl chloroformate in the presence of a base such as Hünig's base (i.e. N,N-diisopropylethylamine) followed by cleavage of the resultant carbamate to yield intermediate compound VI.

Suitably, the solvent employed for carbamate formation may be selected from inert solvents such as, for example, toluene, EDC (ethylene dichloride or 1,2-dichloroethane), MDC (methylene dichloride or 1,2-dichloromethane), xylene; preferably toluene or MDC; most preferably MDC.

The hydrolysis of the carbamate may be carried out by refluxing in an alcohol, for example, methanol, ethanol, isopropyl alcohol, or butanol.

The cyclization of intermediate compound VI may be carried out using acids such as sulphuric acid, para toluene sulphonic acid, methane sulphonic acid, phosphoric acid and hydrochloric acid. The reaction may be carried out in the presence of water, a water miscible solvent or in a mixture thereof. The water miscible solvent may be an alcohol or a ketone.

In accordance with another aspect of the present invention, a process for the synthesis of escitalopram is as shown in Scheme 3, wherein a cyano diol of Formula A is protected and dehydrated to obtain a compound of Formula VII which is then subjected to epoxidation to obtain a compound of Formula VIII. The compound of Formula VIII is finally cyclized, for example under acidic conditions, to obtain escitalopram. The escitalopram may be converted to a salt thereof.

Scheme 3

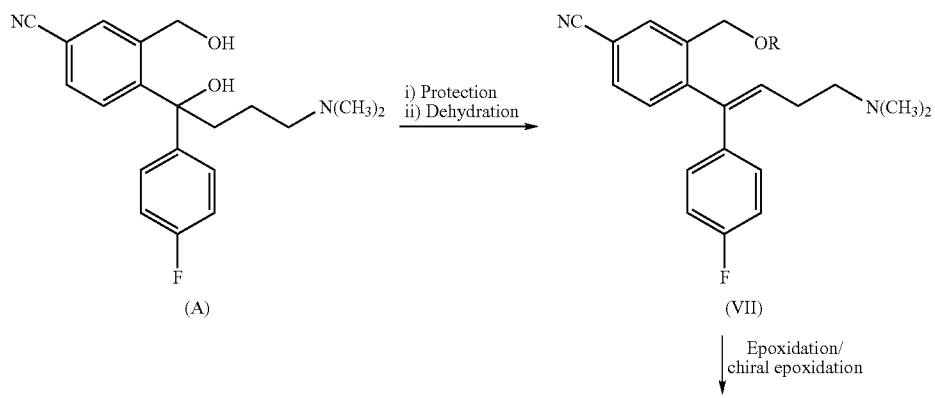

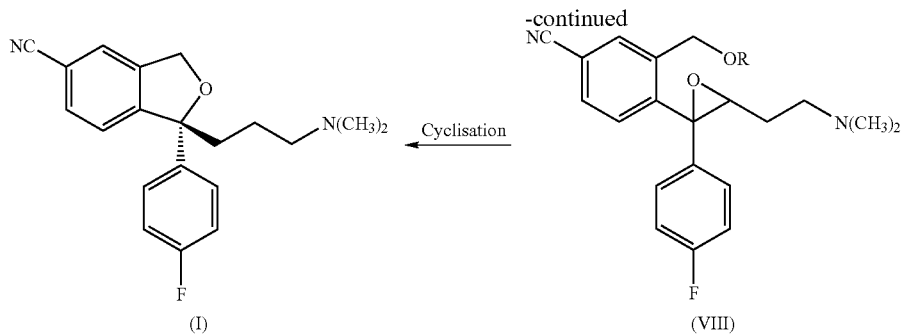

In accordance with still another aspect of the present invention, a process for the synthesis of escitalopram is as shown in Scheme 4, wherein a cyano benzoic acid IX is reacted with a Weinreb amine B in the presence of carbonyl diimidazole to obtain a compound of Formula X, which is reacted with dimethyl propyl amine magnesium chloride to obtain a compound of Formula XI which is further treated with 4-fluoro phenyl magnesium bromide in the presence of taddol C to afford a compound of Formula XII. Compound of Formula XII is further cyclized to obtain escitalopram.

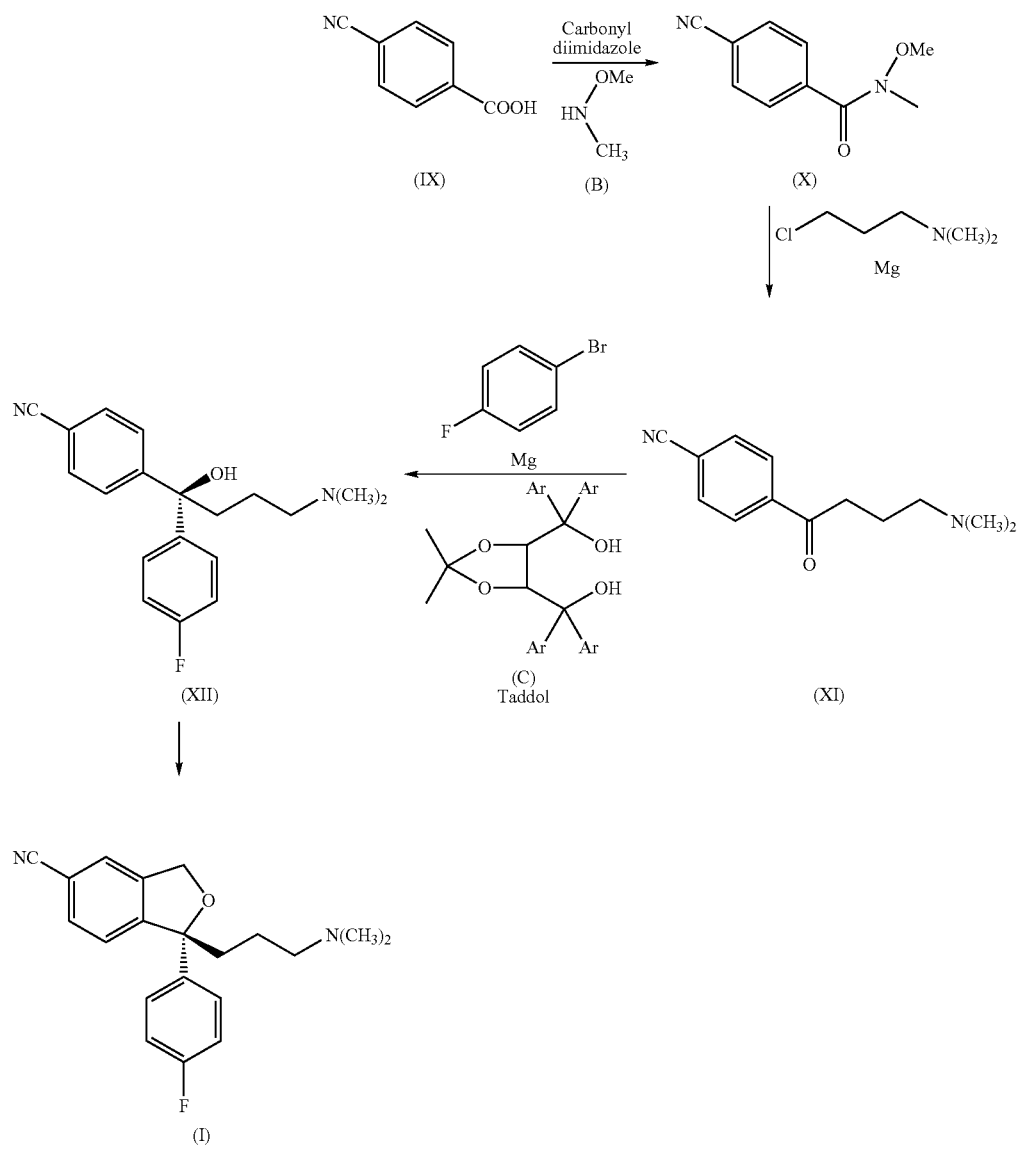

While emphasis has been placed herein on the specific steps of the preferred process, it will be appreciated that many steps can be made and that many changes can be made in the preferred steps without departing from the principles of the invention. These and other changes in the preferred steps of the invention will be apparent to those skilled in the art from the disclosure herein, whereby it is to be distinctly understood that the foregoing descriptive matter is to be interpreted merely as illustrative of the invention and not as a limitation.

EXAMPLES

The details of the invention given in the examples which are provided below are for illustration only and therefore these examples should not be construed to limit the scope of the invention.

Preparation of Citalopram Base

A solution of citalopram hydrobromide (200 Kg, 0.49 kmoles), in toluene (300 lit) and water (200 lit) were stirred at room temperature. The mixture was cooled to 20° C., basified with 10% NaOH solution (100 lit) to pH 9-10 and the phases separated. The aqueous layer was extracted with toluene (2×150 lit). The combined organic solutions were washed with water, dried on sodium sulphate, filtered and used for the next step.

Preparation of Desmethyl Citalopram

The toluene solution containing citalopram base was mixed with 1,2-dichloromethane (400 lit) and cooled to 10-15° C. A solution of 1-chloro ethyl chloroformate (110.8 Kg, 0.77 kmoles) was added to the reaction mass below 20° C. The reaction mass was further stirred for 30 minutes at 15-20° C. Diisopropylethyl amine (30.24 Kg, 0.23 kmoles) was added to the reaction mixture below 20° C. and further stirred for 30 minutes. The temperature of the reaction mass was raised to 60-65° C. and maintained for 2-3 hrs. The reaction mass was diluted with methanol (320 lit) at 60-65° C., heated further for 2-4 hrs at 60-65° C. and evaporated. The reaction mass was cooled to 25-30° C., diluted with water (480 lit) and stirred for 30 minutes. The phases were separated, aqueous layer was extracted with toluene (2×200 lit) and pH of the aqueous layer was adjusted to 9-10 with ammonia solution (320 lit). Toluene (400 lit) was added and the reaction mass stirred for 30 minutes. The organic layer was separated. Aqueous layer was extracted with toluene (2×200 lit). The combined toluene layer was washed with water, followed by brine. The toluene layer was dried on sodium sulphate, filtered and stirred with charcoal (15 Kg). The reaction mass was filtered and evaporated under reduced pressure to afford the title compound. Yield—140 Kg, 91.5%

Preparation of (+)-desmethyl Citalopram DPTTA Salt

Desmethyl citalopram (140 Kg, 0.45 kmoles) was dissolved in isopropyl alcohol (700 lit) at room temperature and heated to 45° C. Di-p-toluoyl-L-tartaric acid (174 Kg, 0.43 kmoles) was added to the reaction mass at 45° C. and stirred further for 2-3 hrs at same temperature. Distilled water (140 lit) was added slowly over 1 hr and stiffing continued for 1 hr more. The reaction mass was cooled to 25-30° C., and solid isolated by filtration. The compound was further purified by crystallization in 6 volumes of isopropyl alcohol:water (isopropyl alcohol:water 5:1) to yield title compound.

Yield=70 Kg, 44.6%
Chiral purity:->99%

Preparation of (+)-desmethyl Citalopram Base

The salt obtained in the previous step, was stirred in a mixture of 1,2-dichloromethane (130 lit) and water (65 lit). The pH of the reaction mass was adjusted to 9-10 by using 10% NaOH solution (~65 lit). The phases were separated. The aqueous layer was extracted with 1,2-dichloromethane (2×100 lit). The combined 1,2-dichloromethane layers were washed with water, dried on sodium sulphate, filtered and evaporated under reduced pressure to afford the title compound.

Preparation of Escitalopram Base

Example 1

Methylation Using Formaldehyde/Formic Acid

The residue obtained in the previous step was stirred in water (210 lit). A solution of formaldehyde (27.25 Kg, 0.9 kmoles) was added to the reaction mass followed by addition of formic acid (15.6 Kg, 0.34 kmoles). The resultant mass was heated 80-90° C., cooled to 25-30° C., and acidified with concentrated hydrochloric acid (30.0 lit). The aqueous layer was washed with toluene (50 lit) and basified with 10% NaOH solution to reach a pH of 9-10 maintaining temperature below 20° C. The reaction mass was stirred with 1,2-dichloromethane (200 lit) and phases were separated. The aqueous layer was extracted with 1,2-dichloromethane (2×100 lit). The combined organic layers were washed with water, dried on sodium sulphate, filtered and evaporated to dryness.

Example 2

Methylation Using Paraformaldehyde/Sodium Borohydride (+)-Desmethyl citalopram base (10 gms, 0.032 moles) was dissolved in 50 ml methanol. A solution of paraformaldehyde (1.16 gms, 0.039 moles) was added to the reaction mass at 25-30° C. and stirred further for 2 hours. The reaction mass was cooled to 0° C. and sodium borohydride (1.47 gms, 0.039 moles) was added maintaining temperature below 5° C. The reaction mass was further stirred for 1 hr at 0-5° C. and evaporated under reduced pressure below 35° C. The residue obtained was stirred in 30 ml water and extracted with 1,2-dichloromethane (3×50 ml). The combined 1,2-dichloromethane layer was washed with water, dried on sodium sulfate, filtered and the clear filtrate was evaporated under reduced pressure below 35° C. to yield the title compound 8.0 gms, 76.55%.

Chiral purity:->99.5%

Preparation of Escitalopram Oxalate

The residue obtained in Example 1 was dissolved in acetone (120 lit) at 25-30° C. A solution of oxalic acid dihydrate (17 Kg, 0.135 kmoles) in acetone (34 lit) was introduced over 30 minutes. The reaction mass was stirred for 2 hrs, cooled to 10° C. and further stirred for 1 hr. The solid obtained was isolated by filtration, washed with acetone (2×40 lit) and dried in a vacuum oven for 4-5 hrs at 50-55° C. to obtain the title compound.

Yield: 40.0 Kg, 98.57%
Chiral purity:->99.5%

Preparation of (+)-desmethyl Citalopram DPTTA Salt Desmethyl citalopram (140 Kg, 0.45 kmoles) was dissolved in isopropyl alcohol (700 lit) at room temperature and heated to 45° C. Di-p-toluoyl-L-tartaric acid (91.22 Kg, 0.225 kmoles) was added to the reaction mass at 45° C. and stirred further for 30 minutes at same temperature. A solution of concentrated hydrochloric acid (22.89 Kg, 0.225 kmoles) was introduced into the reaction mass at 40-45° C. The resultant mixture was stirred at 40-45° C. for 2-3 hrs and at room temperature for 1 hr. The solid obtained was isolated by filtration and washed with isopropyl alcohol. The compound was stirred in 700 liters of isopropyl alcohol at reflux. Distilled water was slowly introduced at reflux temperature until a clear solution was observed. The reaction mass was cooled to room temperature and stirred at 25-30° C. for 1 hr. The solid was isolated by filtration, washed with isopropyl alcohol and dried to yield title compound.

Yield=70 Kg, 43.4%
Chiral purity:->99%

It will be appreciated that the invention may be modified within the scope of the appended claims.

The invention claimed is:

1. A process for preparing a compound of Formula III

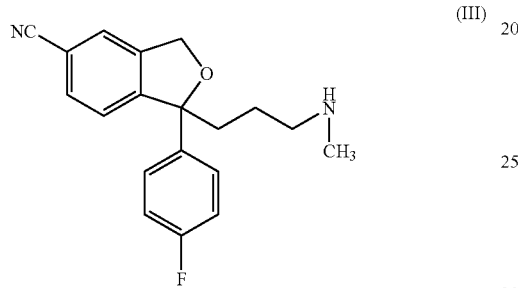

comprising demethylating citalopram of Formula IV

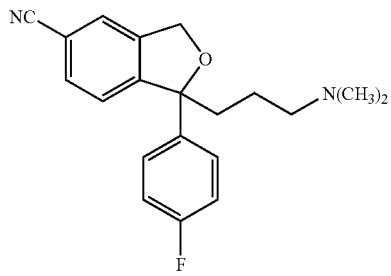

using a chloroformate in the presence of a base to form a carbamate intermediate followed by cleavage of the carbamate intermediate to yield the intermediate compound of Formula III.

2. The process according to claim 1, wherein the chloroformate is an alkyl-, aryl-, substituted-alkyl- or substituted-aryl-chloroformate.

3. The process according to claim 1, wherein the base is N,N-diisopropylethylamine.

4. The process according to claim 3, wherein the solvent employed for carbamate formation is an inert solvent selected from toluene, 1,2-dichloroethane, 1,2-dichloromethane or xylene.

5. The process according to claim 1, wherein the cleavage of the carbamate comprises hydrolysis involving refluxing the carbamate in an alcohol.

6. A process for preparing a compound of Formula II comprising preparing a compound of Formula III according to claim 1, wherein the compound III is in the form of a mixture of the (S)- and (R)- enantiomers, and resolving the mixture of the (S)- and (R)-enantiomers of the compound of Formula III

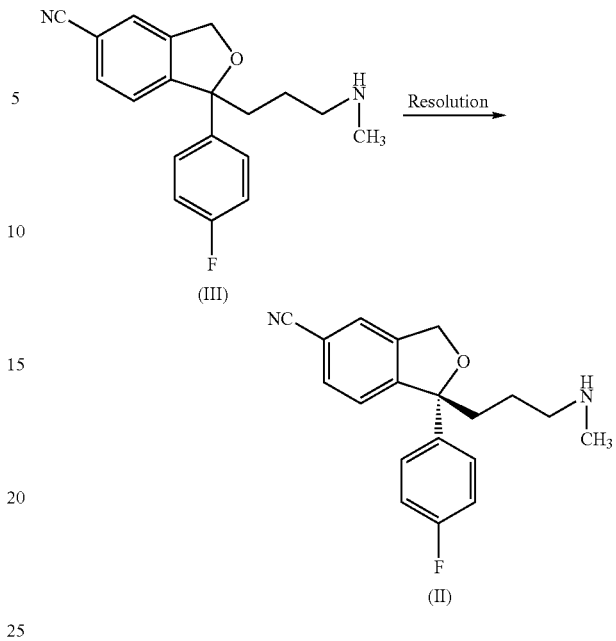

in the presence of a resolving agent.

7. The process according to claim 6, wherein the resolving agent is an enantiomerically pure carboxylic acid.

8. The process according to claim 7, wherein the acid is present in a solvent comprising an alcohol or an alcohol-water mixture.

9. The process according to claim 6, wherein the resolution comprises forming a salt of the S-enantiomer of the compound of Formula III with an acid and converting the salt to the compound of Formula II.

10. The process according to claim 9, wherein the conversion to the free base comprises reaction with a base.

11. The process according to claim 9, wherein the salt of compound III is purified prior to being converted to the compound of Formula II.

12. The process according to claim 6, wherein the resolution is carried out by reacting compound III with a mixture of 0.5 molar equivalence of a carboxylic acid relative to compound III and 0.5 molar equivalence of an inorganic acid relative to compound III.

13. A process for preparing escitalopram or a pharmaceutically acceptable salt thereof, which process comprises preparing a compound of Formula II by a process according to claim 6, methylating the compound of Formula II in the presence of a methylating agent, and optionally converting the escitalopram to the salt thereof.

14. The process according to claim 13, wherein the methylating agent is selected from the group consisting of a combination of formaldehyde and formic acid, a combination of paraformaldehyde and sodium borohydride mixture and a combination of a methyl halide with a base.

15. The process according to claim 13, wherein escitalopram is converted to an acid addition salt thereof selected from the mesylate, besylate, maleate, citrate, tartarate, oxalate, lactate, gluconate, hydrobromide, sulphate or nitrate salt.

16. The process according to claim 15, wherein escitalopram is converted to its oxalate salt.

17. The process according to claim 1 wherein the chloroformate is 1-chloroethylchloroformate.

18. The process according to claim 5 wherein the alcohol is methanol, ethanol, isopropyl alcohol, or butanol.

19. The process according to claim 7 wherein the enantiomerically pure carboxylic acid is di-para toluyl L-tarataric acid.

20. The process according to claim 8 wherein the solvent is an alcohol-water mixture and the alcohol is selected from the group consisting of methanol, ethanol, n-propanol, isopropanol and butanol.

21. The process according to claim 10 wherein the base is sodium hydroxide.

22. The process according to claim 12 wherein the inorganic acid is hydrochloric acid.

* * * * *